(12) United States Patent
Faasch et al.

(10) Patent No.: US 6,221,891 B1
(45) Date of Patent: Apr. 24, 2001

(54) CRYSTAL FORM OF N-(4-TRIFLOUROMETHYLPHENYL)-5-METHYLISOXAZOLE-4-CARBOXAMIDE

(75) Inventors: Holger Faasch, Hochheim; Udo Hedtmann; Uwe Westenfelder, both of Frankfurt; Erich Paulus, Eppstein, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/428,499

(22) Filed: Oct. 28, 1999

Related U.S. Application Data

(62) Division of application No. 09/129,783, filed on Aug. 6, 1998, now Pat. No. 6,060,494.

(30) Foreign Application Priority Data

Aug. 8, 1997 (DE) ............................... 197 34 438
Dec. 17, 1997 (DE) ............................... 197 56 093

(51) Int. Cl.⁷ ........................ A61K 31/42; C07D 261/18
(52) U.S. Cl. ............................. 514/378; 548/248
(58) Field of Search ............................. 548/248; 514/378

(56) References Cited

U.S. PATENT DOCUMENTS

| | | | |
|---|---|---|---|
| 4,061,767 | 12/1977 | Ertel et al. ............................. | 424/282 |
| 4,284,786 | 8/1981 | Kämmerer et al. ..................... | 548/248 |
| 4,351,841 | 9/1982 | Kämmerer et al. ..................... | 424/272 |
| 4,521,431 | 6/1985 | Crookes ................................. | 514/471 |
| 4,935,434 | 6/1990 | Han ........................................ | 514/378 |
| 5,371,099 | 12/1994 | Bartlett et al. ......................... | 514/378 |
| 5,476,866 | 12/1995 | Kuo et al. .............................. | 514/378 |
| 5,494,911 | 2/1996 | Bartlett et al. ......................... | 514/256 |
| 5,506,249 | 4/1996 | Kuo et al. .............................. | 514/378 |
| 5,583,150 | 12/1996 | Robertson et al. .................... | 514/378 |
| 5,728,721 | 3/1998 | Bartlett ................................... | 514/378 |
| 5,886,033 | 3/1999 | Schwab et al. ........................ | 514/321 |

FOREIGN PATENT DOCUMENTS

| | | |
|---|---|---|
| 25 24 959 A1 | 12/1976 | (DE) . |
| 41 27 737 A1 | 2/1993 | (DE) . |
| 0 013 376 A2 | 7/1980 | (EP) . |
| 0 617 959 A1 | 10/1994 | (EP) . |
| WO 91/17748 | 11/1991 | (WO) . |

*Primary Examiner*—Deborah C. Lambkin
(74) *Attorney, Agent, or Firm*—Finnegan, Henderson, Farabow, Garrett & Dunner, L.L.P.

(57) ABSTRACT

The invention relates to a crystal modification of the compound of the formula I

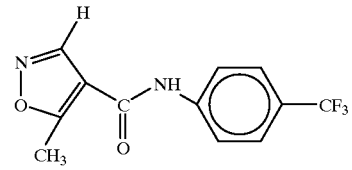

(I)

and the processes for the preparation of and use that crystal modifications 1. The invention is used for treating acute immunological episodes, such as sepsis, allergies, graft-versus-host and host-versus-graft-reactions, autoimmune diseases, in particular rheumatoid arthritis, systemic lupus erythematosus, multiple sclerosis, psoriasis, atopic dermatitis, asthma, urticaria, rhinitis, uveitis, type II diabetes, liver fibrosis, cystic fibrosis, colitis, cancers, such as lung cancer, leukemia, ovarian cancer, sarcomas, Kaposi's sarcoma, meningioma, intestinal cancer, lymphatic cancer, brain tumors, breast cancer, pancreatic cancer, prostate cancer, or skin cancer.

10 Claims, 3 Drawing Sheets

CRYSTAL FORM OF N-(4-TRIFLOUROMETHYLPHENYL)-5-METHYLISOXAZOLE-4-CARBOXAMIDE

This is a division of application Ser. No. 09/129,783, filed Aug. 6, 1998, U.S. Pat. No. 6,060,404, which is incorporated herein by reference.

This case claims benefit under 35 U.S.C. § 119 of German priority document 19734438.0 filed on Aug. 8, 1997. This document, as well as German priority document 19756093.8, filed Dec. 17, 1997, are hereby incorporated by reference.

The invention relates to a novel readily soluble crystal modification (hereafter referred to as "the first crystal modification") of the compound of formula I

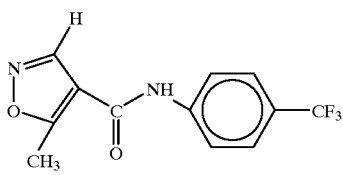

(I)

in which the transmission X-ray diffraction pattern obtained with a focusing Debye-Scherrer beam and Cu—$K_{\alpha 1}$-radiation, has lines at the following diffraction angles 2θ:

Lines of strong intensity: 10.65; 14.20; 14.80; 16.10; 21.70; 23.15; 24.40; 24.85; 25.50; 25.85; 26.90; and 29.85 degrees, Lines of medium intensity: 7.40; 9.80; 13.10; 15.45; 16.80; 20.70; 21.45; 22.80; 23.85; 27.25; and 28.95 degrees,

Figure 1:
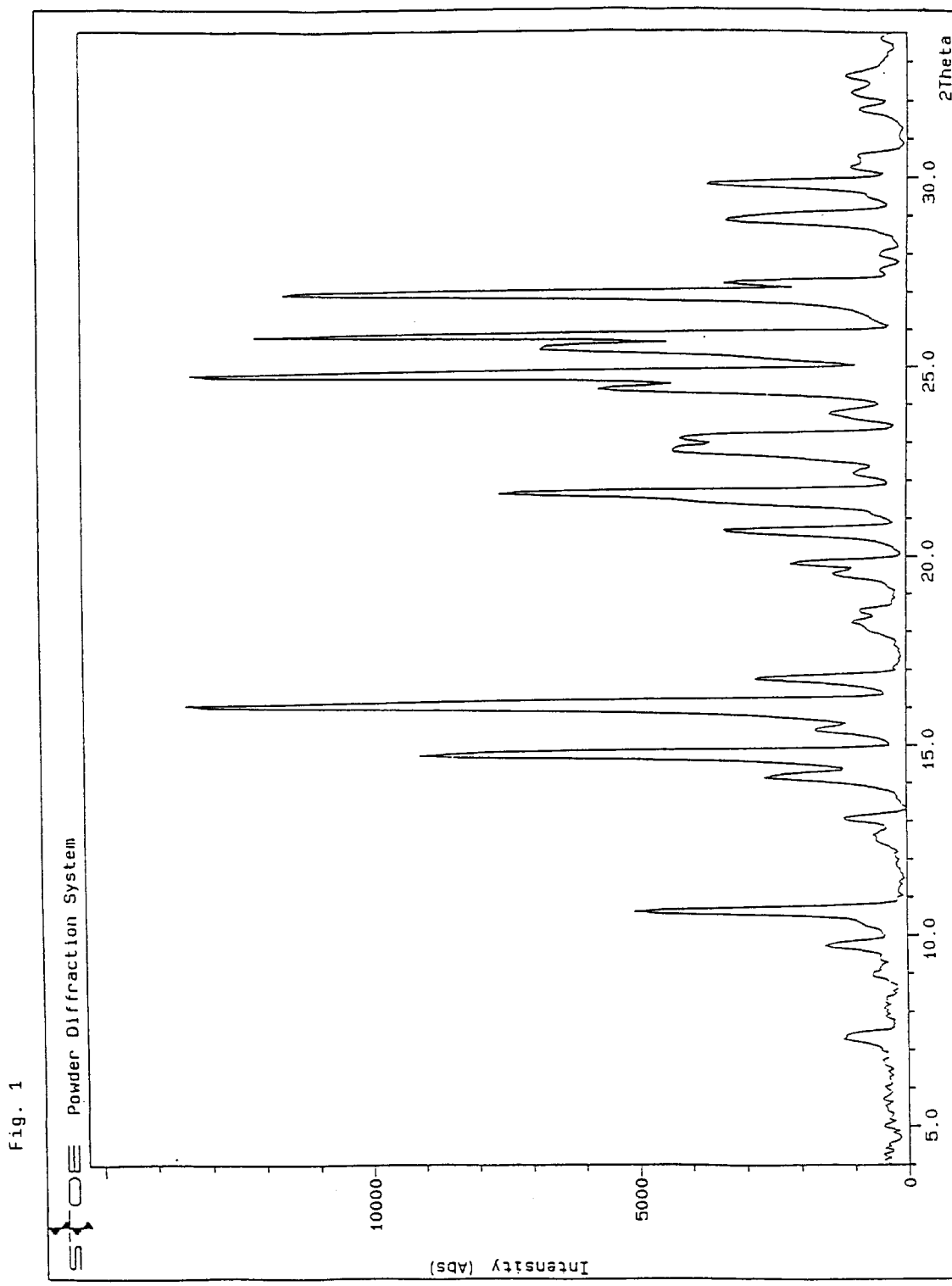
FIG. 1 is the X-ray diffraction pattern of the first crystal modification.

The X-ray diffraction pattern of the first crystal modification recorded using Cu—$K_{\alpha 1}$ radiation is shown in FIG. 1. The pattern was recorded using the STADI P two-circle diffractometer from Stoe (Darmstadt, Germany) and the computer-assisted single crystal diffractometer R3 m/V from Siemens (radiation used: $MoK_{\alpha}$).

The infrared spectrum of the first crystal modification of the compound of formula I (1 mg in 300 mg of KBr) recorded using an infrared spectrophotometer shows the following main bands (units: $cm^{-1}$):

| | | | |
|---|---|---|---|
| 1321 | 1481 | 672 | 3201 |
| 1607 | 3355 | 763 | 701 |
| 1109 | 1264 | 908 | 948 |
| 1065 | 1384 | 754 | 511 |
| 1536 | 1361 | 592 | 733 |
| 1663 | 852 | 427 | 960 |
| 1241 | 1014 | 3111 | 1779 |
| 1410 | 3297 | 3065 | 1811 |
| 1160 | 877 | 3221 | 484 |
| 1691 | 940 | 974 | 3442 |
| 831 | 3274 | 3129 | 3434 |
| 1188 | 894 | 628 | |

Figure 3:
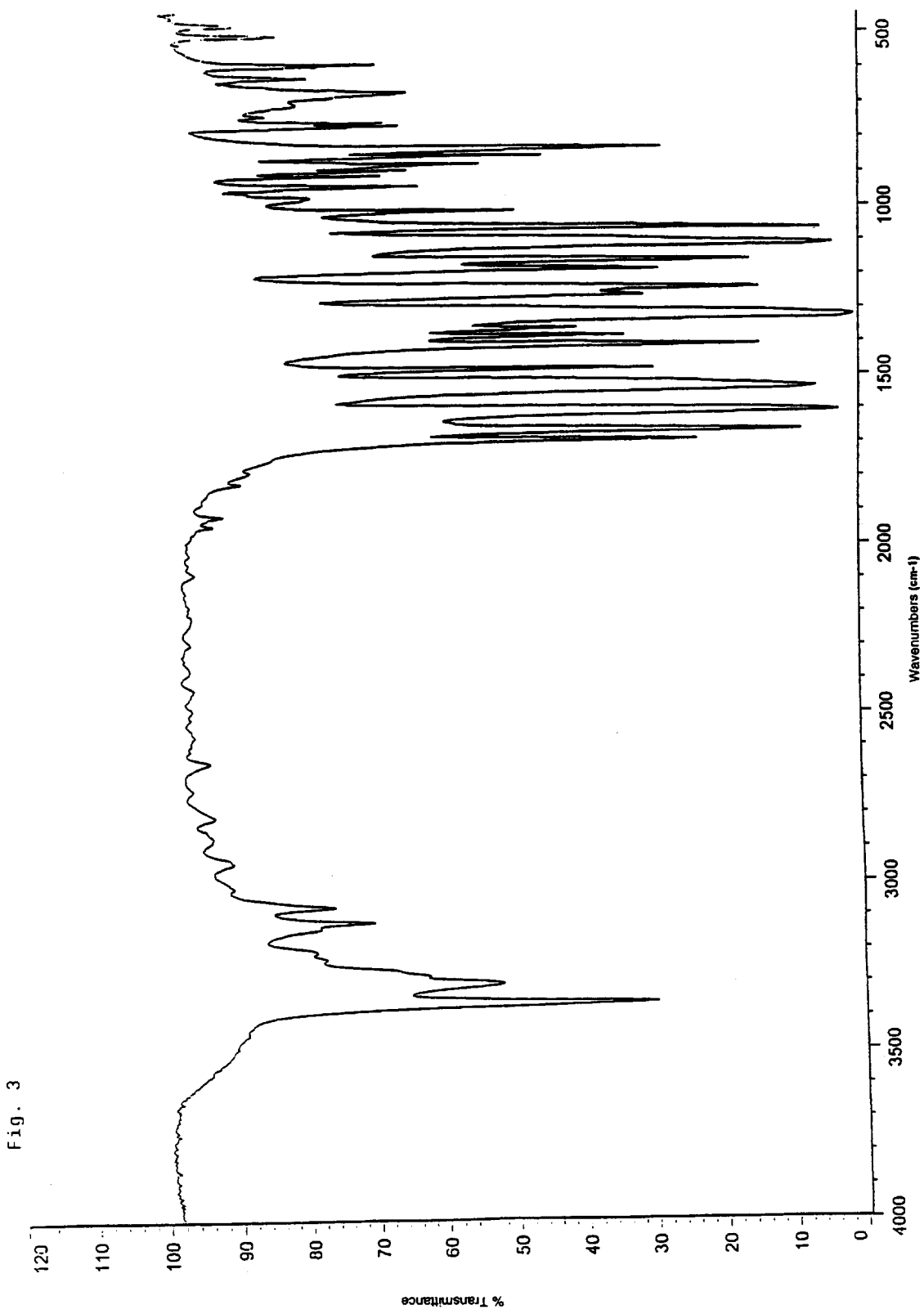
FIG. 3 is the infrared spectrum of the first crystal modification.

The stated wavenumbers are arranged in ascending intensity. The infrared spectrum of the first crystal modification of the compound of formula I according to Example 1 shown in FIG. 3, the transmittance in % being stated along the ordinate and the wavenumber in $cm^{-1}$ along the abscissa.

The compound of formula I crystallizes in the first crystal modification in the space group $P2_1/c$ with 8 molecules in the unit cell. Molecules of the compound of formula I are present as dimers which originate from the individual molecules by formation of a —C=O . . . HN hydrogen bridge bond (2.938 Å), the two molecular levels being virtually perpendicular to one another (91.2°). The two molecules have very different conformations. The angles made by the five- and six-membered rings with the central carbonyl group are 5.4° and 2.1° and 23.4° and 23.1°, respectively. The latter twist creates the steric preconditions permitting the hydrogen bridge bond between the two molecules.

Figure 2:
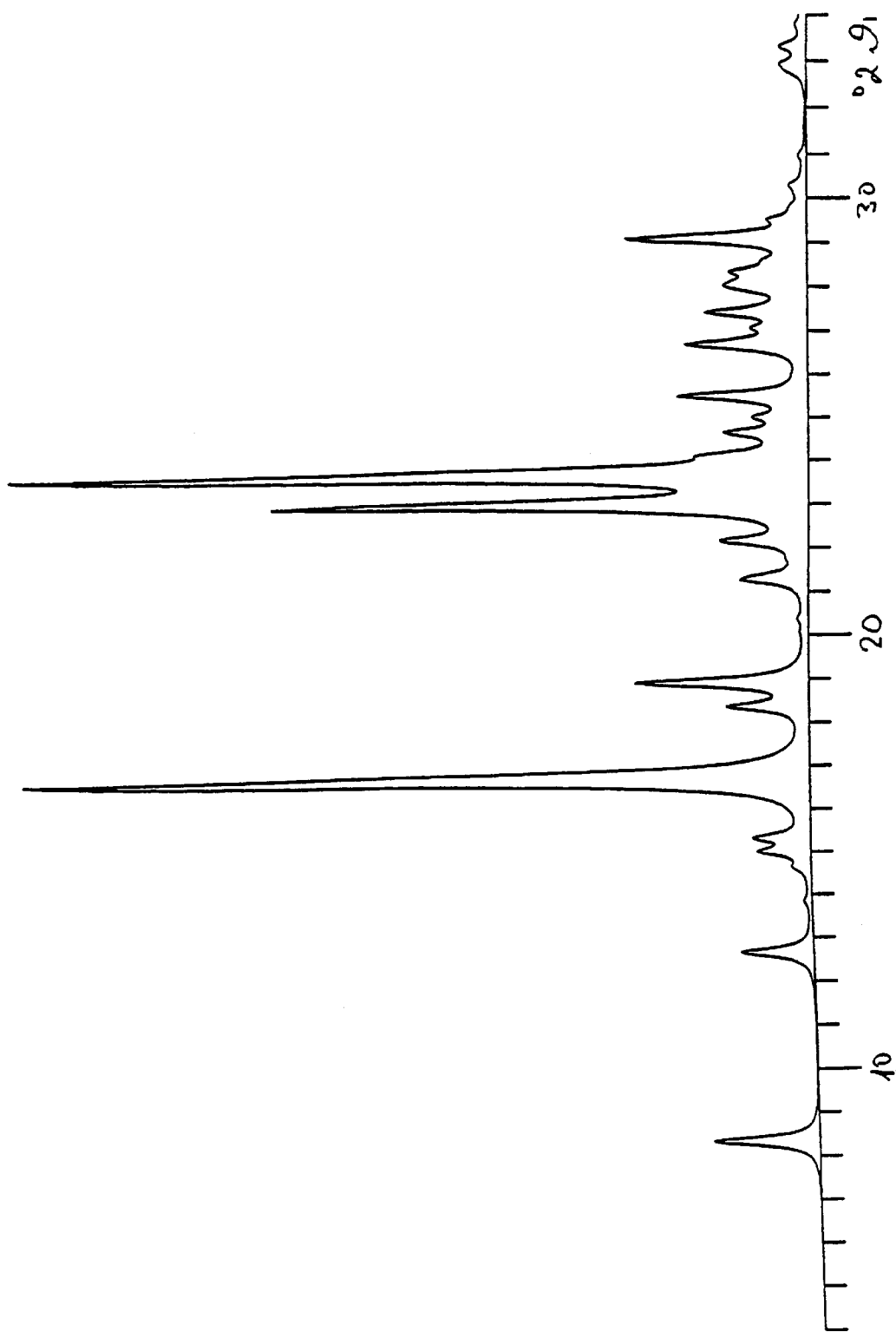
FIG. 2 is the X-ray diffraction pattern of the second crystal modification.

The compound of formula I is known per se and is also referred to as Leflunomide (HWA 486). It can be obtained in the manner described in U.S. Pat. No. 4,284,786. However, the crystals prepared by recrystallization from, for example, toluene are obtained in a crystal form called the second crystal modification. The X-ray diffraction pattern (Cu—$K_{\alpha 1}$ radiation) of the second crystal modification is shown in FIG. 2 and has characteristic lines at the following diffraction angles 2θ:

Lines of strong intensity: 16.70; 18.90; 23.00; 23.65; and 29.05 degrees.

Lines of medium intensity: 8.35; 12.65; 15.00; 15.30; 18.35; 21.25; 22.15; 24.10; 24.65; 25.45; 26.65; 27.40; 28.00; and 28.30 degrees.

The compound of formula I crystallizes in the second crystal modification in the space group $P2_1/c$ with 4 molecules in the unit cell. The molecule is essentially planar. The angle between the planar groups of atoms is less than 2.4°. The molecules are arranged in stacks in the crystal. The molecules lie in stacks adjacent to one another and are arranged in an antiparallel manner. Very weak hydrogen bridge bonds link the dimers in the crystal (NH . . . N: 3.1444 Å). The C=O group is not involved in any hydrogen bridge bonding.

The X-ray diffraction patterns furthermore permit the determination of the amount of the first crystal modification in a mixture containing both modifications. The line at 2θ=8.350° of the second crystal modification and the line at 2θ=16.1° of the first crystal modification are suitable for the quantitative determination. If the ratio of the peak heights is calculated and is correlated with the content of the modification, a calibration line is obtained. The limit of detection of this method is about 0.3% of the first crystal modification in crystals containing the second crystal modification.

The first crystal modification has better water solubility than the second crystal modification. At 37° C., 38 mg/l of the first crystal modification can be dissolved whereas 25 mg/l of the second crystal modification go into solution. Furthermore, the first crystal modification is stable in the temperature range from −15° C. to +40° C., preferably from 20° C. to 40° C., and is not converted into the second crystal modification under these conditions.

The first crystal modification, according to the invention, of the compound of formula I is obtained, for example, by heating a suspension of crystals of the second crystal modification or mixtures of the second crystal modification and the first crystal modification of the compound of formula I in a solvent to a temperature of from about 10° C. to about 40° C., preferably from about 150° C. to about 30°C., in particular from about 20° C. to about 25° C. The preparation rate is essentially dependent on the temperature. Solvents in which the compound of formula I are poorly soluble are advantageously used. For example, it is possible to use water or aqueous solutions containing ($C_1$–$C_4$) alcohols (e.g., methanol, ethanol, propanol, isopropanol, butanol or isobutanol) and/or ketones, such as acetone or methyl ethyl ketone, or mixtures thereof. As a rule, the heating is carried out in aqueous suspension, expediently while stirring or shaking. The heat treatment is carried out until through this process the second crystal modification is completely converted into the first crystal modification.

The complete conversion of the second crystal modification to the first crystal modification is dependent on the temperature and, as a rule, takes from 36 hours to 65 hours, preferably from 48 hours to 60 hours, at a temperature of 20° C. The reaction is monitored by X-ray diffraction or IR spectroscopy by means of samples taken during the treatment.

A further process for the preparation of the first crystal modification of the compound of formula I comprises dissolving the second crystal modification or mixtures of the first and second crystal modifications in a solvent and then cooling the solution abruptly to temperatures of from about −5°C. to about −25° C. The terms "solution" and "suspension" are used interchangeably throughout and are meant to include circumstances where a solid or solids is placed in a solvent or a mixture of solvents regardless of solubility. Suitable solvents are, for example, water-miscible solvents such as ($C_1$–$C_4$) alcohols, as well as ketones, such as acetone or methyl ethyl ketone, or other solvents, such as ethyl acetate, toluene dichloromethane or mixtures thereof. The dissolution process takes place at room temperature of from about 20° C. to about 25° C. or at elevated temperatures up to the boiling point of the solvent under atmospheric pressure or under superatmospheric or reduced pressure. The solution obtained is, if required, filtered in order to separate off undissolved components or crystals from Leflunomide. The filtered solution is then cooled so rapidly that only crystals of the first crystal modification form. An adequate cooling process comprises, for example, introducing the filtered solution into a vessel which has been cooled to −15° C. or spraying filtered solution into a space cooled to −10° C. or cooling the solution under vacuum condensation conditions.

The preferred process comprises introducing the compound of formula I into methanol and carrying out the dissolution process at the boiling point of methanol at atmospheric pressure or reduced pressure, then filtering the hot solution and transferring the filtered solution to a vessel which has been cooled to −15° C., the transfer being effected so slowly that the temperature of the crystal suspension obtained does not increase to more than −10° C. The precipitated crystals are then washed several times with methanol and are dried under reduced pressure.

The crystallization can be carried out without seeding with crystals of the first crystal modification; however seeding with crystals of the first crystal modification is the preferred method. The seeding is effected in the cooled vessel. The amount of seed material depends on the amount of the solution and can be easily determined by a person of ordinary skill in the art. The aforementioned processes are also suitable for converting mixtures containing the first and second crystal modifications into an essentially pure the first crystal modification of the compound of formula I.

The invention also relates to novel processes for the preparation of the second crystal modification of formula I. By means of novel processes, it is also possible to convert mixtures containing the first and second crystal modifications specifically into the second crystal modification. For this purpose, for example, crystals of the first crystal modification, or mixtures of the first and second crystal modifications are dissolved in a solvent. Suitable solvents are, for example, water-miscible solvents such as $C_1$–$C_4$ alcohols (e.g., methanol, ethanol, propanol, isopropanol, butanol or isobutanol), as well as ketones such as acetone or methyl ethyl ketone, or mixtures thereof. Mixtures of organic solvents with water, for example of about 40% to about 90% of isopropanol, have also proven useful.

The dissolution process is preferably carried out at elevated temperature up to the boiling point of the respective solvent. The hot solution is kept at the boiling point for some time in order to ensure complete dissolution of the compound of formula I. The filtered solution is then cooled so slowly that only crystals of the second crystal modification form. Cooling is preferably effected to final temperatures of about 20° C. to about −10° C., in particular to temperatures of about 10° C. to about −5° C., very particularly preferably to temperatures of from about 10° C. to about 5° C. The crystals are separated off and washed with isopropanol and then with water. The substance is dried at elevated temperature, preferably at about 60° C. under reduced pressure or at atmospheric pressure.

A preferred process for preparing the second crystal modification comprises dissolving the compound of formula I in an about 80% strength isopropanol at the boiling point of isopropanol and at atmospheric pressure or under reduced pressure and then cooling the hot solution so slowly that the crystallization takes place at temperatures of more than about 40° C., preferably from about 40° C. to about 85° C., particularly preferably from about 45° C. to about 80° C., in particular from about 50° C. to about 70° C. The precipitated crystals are then washed several times with isopropanol and are dried under reduced pressure. The crystallization can be carried out without seeding with crystals of the second crystal modification or preferably in the presence of crystals of the second crystal modification, which are introduced by seeding into the solution containing the compound of formula I. Seeding may also be carried out several times at different temperatures. The amount of the seed material depends on the amount of the solution and can be readily determined by a person of ordinary skill in the art.

A particularly preferred process for the preparation of the compound of formula I in the second crystal modification comprises
a) transferring the compound of formula I where no the second crystal modification is present or mixtures of the second crystal modification and other crystal forms of the compound of formula I into an organic solvent or into mixtures of organic solvents and water,
b) heating the mixture obtained to a temperature greater than about 40° C. to about the boiling point of the organic solvent,
c) diluting the resulting solution with water or distilling off organic solvent so that the organic solvent and the water are present in a ratio of from 4:1 to 0.3:1 and
d) carrying out the crystallization at temperatures above about 40° C. (The solution obtained is preferably filtered after process step b).

By means of the particularly preferred process, it is also possible to convert mixtures containing the first and second crystal modifications specifically into the second crystal modification. For this purpose, crystals of the first crystal modification or mixtures of the first and second crystal modifications are dissolved in a mixture containing organic solvents and water. Suitable solvents are, for example, water-miscible solvents such as $C_1$–$C_4$ alcohols (e.g., methanol, ethanol, propanol, isopropanol, butanol or isobutanol), as well as ketones such as acetone or methyl ethyl ketone, or mixtures thereof.

Advantageous mixtures contain organic solvent and water in a ratio of from about 1:1 to about 8:1, preferably from about 2:1 to about 6:1, and in particular from about 3:1 to about 5:1.

The preparation of the solution is preferably carried out at elevated temperature, in particular at temperatures of from about 41° C. to the boiling point of the respective organic solvent. The heated solution is, for example, kept for some time at the boiling point in order to ensure complete dissolution of the compound of formula I. The dissolution process can also be carried out at superatmospheric pressure. The solution is then filtered. The filter used has a pore diameter of from about 0.1 µm to about 200 µm. Advantageously, water which has the same temperature as the filtered solution is then added to the filtered solution, or the organic solvent is distilled off. The solutions obtained advantageously contain the organic solvent and water in a ratio of from about 4:1 to about 0.3:1, preferably from about 2:1 to about 0.6:1, particularly preferably from about 1.6:1 to about 0.8:1. Cooling is then carried out slowly to a minimum temperature of about 40° C. and crystals form. The crystals are separated off and are washed with isopropanol and then with water and, advantageously, dried at elevated temperature, preferably at about 60° C., under reduced pressure or at atmospheric pressure.

A particularly preferred process comprises dissolving the compound of formula I in a mixture of isopropanol and water in a ratio of from about 4:1 to about 5:1 and at the boiling point of isopropanol under atmospheric pressure or reduced pressure and filtering the solution preferably, a filter pore of lumen diameter is used. Thereafter, water at the same temperature is added to the hot solution in an amount such that a ratio of isopropanol to water is from about 2:1 to about 0.8:1. The crystallization is then carried out at temperatures of more than about 40° C., preferably from about 40° C. to about 85° C., particularly preferably from about 45° C. to about 80° C., in particular from about 50° C. to about 70° C. The crystals are then washed several times with isopropanol and are dried under reduced pressure.

A further process for the preparation of the second crystal modification from the first crystal modification or from a mixture containing the first and second crystal modifications comprises heating the solid forms to a temperature of from above about 40° C. to about 130° C., preferably from about 50° C. to about 110° C., in particular from about 70° C. to about 105° C., very particularly preferably about 100° C. The conversion of the first crystal modification into 1 is dependent on the temperature and, for example at about 100° C., takes from 2 to 5 hours, preferably from 2 to 3 hours.

A further process for the preparation of the second crystal modification comprises preparing a suspension containing crystals of the first crystal modification or a mixture of crystals containing the first and second crystal modifications and a solvent.

The second crystal modification of the compound of formula I is obtained by heating the suspension of the crystals in a solvent to a temperature of more than about 40° C., preferably from about 41° C. to about 100° C., in particular from about 50° C. to about 70° C. The preparation is essentially dependent on temperature. Advantageous solvents are those in which the compound of formula I has poor solubility. For example, it is possible to use water or aqueous solutions containing $C_1$–$C_4$ alcohols, ketones, such as methyl ethyl ketone or acetone, or a mixture thereof. As a rule, the heating is effected in an aqueous suspension, expediently while stirring or shaking. The heat treatment is carried out until the first crystal modification has been significantly converted into the second crystal modification.

The conversion of the first crystal modification into the second crystal modification is dependent on the temperature and, as a rule, takes from 20 hours to 28 hours, preferably 24 hours, at a temperature of 50° C. The reaction is monitored by X-ray diffraction or IR spectroscopy by means of samples taken during the treatment.

The first crystal modification, according to the invention, of the compound of formula I is suitable, for example, for the treatment of acute immunological episodes, such as sepsis, allergies, graft-versus-host- and host-versus-graft-reactions autoimmune diseases, in particular rheumatoid arthritis, systemic lupus erythematosus, multiple sclerosis psoriasis, atopic dermatitis, asthma, urticaria, rhinitis, uveitis type II diabetes liver fibrosis, cystic fibrosis, colitis cancers, such as lung cancer, leukemia, ovarian cancer, sarcomas, Kaposi's sarcoma, meningioma, intestinal cancer, lymphatic cancer, brain tumors, breast cancer, pancreatic cancer, prostate cancer or skin cancer.

The invention also relates to drugs comprising an effective content of the first crystal modification of the compound of formula I together with a pharmaceutical excipient, additive and/or additional active ingredients and adjuvants.

The drugs according to the invention, comprising an effective content of the first crystal modification of the compound of formula I, have the same efficacy in humans who suffer from rheumatic arthritis in comparison with the treatment with a drug comprising an effective content of the second crystal modification of the compound of formula I.

The invention furthermore relates to a process for the preparation of the drug, which comprises processing the first crystal modification of the compound of formula I and a pharmaceutical excipient to give a pharmaceutical dosage form.

The drug according to the invention may be present as a dosage unit in dosage forms such as capsules (including microcapsules), tablets (including sugar-coated tablets, pills) or suppositories, the capsule material performing the function of the excipient where capsules are used and it being possible for the content to be present, for example, as a powder, gel, emulsion, dispersion or suspension. However, it is particularly advantageous and simple to prepare oral (peroral) formulations containing the first crystal modification of the compound of formula I, which contain the calculated amount of the active ingredient together with a pharmaceutical excipient. An appropriate formulation (suppository) for rectal therapy may also be used. Transdermal application in the form of ointments or creams or oral administration of tablets or suspensions which contain the formulation according to the invention is also possible.

In addition to the active ingredients, ointments, pastes, creams, and powders may contain conventional excipients, for example, animal and vegetable fats, waxes, paraffins, starch, tragacanth, cellulose derivatives, polyethylene glycols, silicones, bentonites, talc, zinc oxide, lactose, silica, aluminum hydroxide, calcium silicate, polyamide powder, or a mixture of these substances.

The tablets, pills or granules can be prepared by conventional processes, such as compression, immersion, or fluidized-bed processes, or by coating in a pan, and contain excipients and other conventional adjuvants, such as gelatine, agarose, starch (for example potato, corn or wheat starch) cellulose, such as ethyl cellulose, silica, various sugars, such as lactose, magnesium carbonate and/or calcium phosphates. The sugar-coating solution usually comprises sugar and/or starch syrup and generally also contains gelatine, gum Arabic, polyvinylpyrrolidone, synthetic cellulose esters, surfactants, plasticizers, pigments, and similar additives according to the prior art. Any conventional flow regulators, lubricants, such as magnesium stearate, and external lubricants may be used for the preparation of the formulations.

The dosage to be used is of course dependent on various factors, such as the host be treated (i.e., human or animal), age, weight, general state of health, the severity of the symptoms, the disease to be treated, the type of accompanying treatment with other drugs, or the frequency of the treatment. The doses are administered in general several times per day and preferably once to three times per day.

A suitable therapy therefore comprises, for example, administering one, two or 3 single doses of a formulation containing N-(4-trifluoromethylphenyl)-5-methylisoxazole-4-carboxamide in The first crystal modification in an amount of from 2 to 150 mg, preferably from 10 to 100 mg, in particular from 10 to 50 mg.

The amount of the active ingredients does of course depend on the number of single doses and also on the disease to be treated. The single dose may also comprise a plurality of simultaneously administered dosage units.

EXAMPLE 1
Preparation of the First Crystal Modification

About 40 mg of the compound of formula I, prepared according to U.S. Pat. No. 4,284,786, were shaken with 40 ml of water in bottles (volume 45 ml). The shaking of the closed bottles was carried out at 15° C.–25° C. in a water bath. After 48 hours, a sample was taken, filtered and dried and a powder X-ray diffraction pattern was prepared. The measurement was carried out using the STADI P two-circle diffractometer from Stoe (Darmstadt, Germany) with Cu—$K_{\alpha 1}$ radiation by the Debye-Scherrer method under transmission conditions.

FIG. 1 shows the resulting X-ray diffraction pattern and is typical of the first crystal modification of the compound of formula I.

EXAMPLE 2

| Solubility in water | |
|---|---|
| Apparatus | flask, magnetic stirrer, water bath 37° C. ± 0.5° C. |
| Medium | water (+37° C.) |
| Sampling | 5 hours |
| Preparation | First and second crystal modifications according to Examples 1 and 2 were transferred to water and stirred vigorously at 37° C. |
| Detection | UV spectroscopy at a wavelength of 258 µm |
| Result: | |
| Second crystal modification | 25 mg dissolved in 1 liter of water at 37° C. |
| First crystal modification | 38 mg dissolved in 1 liter of water at 37° C. |

EXAMPLE 3
Stability of the First Crystal Modification

Samples of The first crystal modification were prepared as in Example 1 and were stored at various temperatures at atmospheric humidity. After the stated times, samples were taken and an X-ray diffraction pattern was prepared as in Example 1. Table 1 shows the results.

TABLE 1

| Time (Months) | Storage conditions | Crystal modification |
|---|---|---|
| 1 | −15° C. | First |
| 3 | −15° C. | First |
| 6 | −15° C. | First |
| 1 | +25° C. | First |
| 3 | +25° C. | First |
| 6 | +25° C. | First |
| 1 | +40° C. | First |
| 3 | +40° C. | First |
| 6 | +40° C. | First |

TABLE 1-continued

| Time (Months) | Storage conditions | Crystal modification |
|---|---|---|
| 1 | +40° C./75% relative humidity | First |
| 3 | +40° C./75% relative humidity | First |
| 6 | +40° C./75% relative humidity | First |
| 1 | +60° C. | about 76% Second |
| 3 | +60° C. | Second |

[1]) A calibration curve was used for the determination of the second crystal modification.

For preparing the calibration curve for the quantitative determination, the reflection at 2θ=8.35° was used for phase 1 and the reflection at 2θ=16.1° was used for phase 2. The ratios of the corresponding peak heights were calculated and were correlated with the contents of phase 2. The limit of the method is 0.3%. The sample after storage for 1 month at 60° C. contains about 76% of the second crystal modification according to this method.

EXAMPLE 4
Preparation of the Second Crystal Modification

Water-moist crude Leflunomide is first dissolved in isopropanol/water (corresponding to 16 kg of crude, dry Leflunomide in 28 l of isopropanol plus the amount of water which, together with the water content of the moist product, gives a total amount of water of 9 l).

The mixture is then heated to 78° C. to 82° C., stirred at this temperature for 25 minutes (min) and then filtered through a pressure funnel into a vessel also already heated to the same temperature. The pressure filter is rinsed with an amount of isopropanol which, together with isopropanol used (iPrOH), gives an iPrOH/water ratio of 4:1 (in this case 4 l). Thereafter, water also preheated to 78° C. to 82° C. is added (32 l, gives iPrOH/water=0.8:1). The solution already becomes cloudy and is then cooled to about 65°C. in 20 min, kept at this temperature for about 40 min, then cooled to about 40°C. in 70 min and stirred for a further 20 min. The product is isolated by centrifuging.

Table 2 shows the results of 4 batches.

TABLE 2

| Batch | Initial concentration [g/l] | iPrOH/H$_2$O ratio | Final concentration [g/l] | Proportion* of crystals of The first crystal modification [%] | Yield [%] |
|---|---|---|---|---|---|
| 1 | 600 | 4:1 | 600 | n.d. | 73.2 |
| 2 | 600 | 3:1 | 563 | <0.4 | 71.4 |
| 3 | 400 | 2:1 | 333 | <0.4 | 70.5 |
| 4 | 400 | 0.8:1 | 222 | <0.4 | 85.6 |

*The determination was carried out by X-ray powder diffractometry; the proportion of the first crystal modification was always below the limit of detection, which was about 0.4%.
n.d. means not determined The present invention may be embodied in other specific forms without departing from it spirit or essential characteristics. The described embodiments are to be considered in all respects only as illustrative and not restrictive. The scope of the inventions, therefore, indicated by the appended claims rather than by the foregoing description. All changes which come within the meaning and range of equivalency of claims are to be embraced within their scope.

What is claimed is:
1. A composition comprising a first crystal modification of a compound of the formula (I):

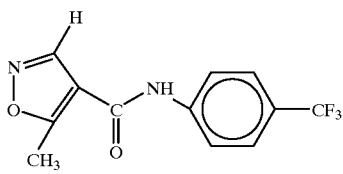

(I)

which has a transmission X-ray diffraction pattern obtained with a focusing Debye-Scherrer beam and Cu—$K_{\alpha 1}$-radiation, having the following diffraction angles 2θ:

Lines of strong intensity: 10.65; 14.20; 14.80; 16.10; 21.70; 23.15; 24.40; 24.85; 25.50; 25.85; 26.90; and 29.85 degrees, Lines of medium intensity: 7.40; 9.80; 13.10; 15.45; 16.80; 20.70; 21.45; 22.80; 23.85; 27.25; and 28.95 degrees.

2. A composition according to claim 1 further comprising at least one excipeint.

3. A composition according to claim 2 wherein the excipient is selected from at least one of starch, gelatine, agarose, cellulose, silica, a sugar, magnesium carbonate, calcium phosphate, and a combination thereof.

4. A composition according to claim 3 wherein the starch is selected from potato starch, corn starch, and wheat starch.

5. A composition according to claim 3 wherein the cellulose is ethyl cellulose.

6. A composition according to claim 3 wherein the sugar is lactose.

7. A composition according to claim 2 in a finished dosage form selected from tablets, granules, and capsules.

8. A composition of claim 2 wherein at least one excipient is a lubricant.

9. A composition comprising a first crystal modification of Leflunomide and a second crystal modification of Leflunomide.

10. A composition according to claim 9 wherein said first crystal modification has x-ray diffraction lines at about the following angles 2θ: 10.65, 14.20, and 14.80.

* * * * *